United States Patent
Yoon et al.

(10) Patent No.: US 7,892,658 B2
(45) Date of Patent: *Feb. 22, 2011

(54) COMPOUND AND ORGANIC LIGHT EMITTING DEVICE USING THE SAME

(75) Inventors: Seok Hee Yoon, Daejeon Metropolitan (KR); Jae Min Moon, Daejeon Metropolitan (KR); In Ho Hwang, Daejeon Metropolitan (KR); Min Jeong Lee, Seoul (KR); Wook Dong Cho, Daejeon Metropolitan (KR); Ji Eun Kim, Daejeon Metropolitan (KR); Byung Sun Jeon, Seoul (KR)

(73) Assignee: LG Chem, Ltd., Seoul (KR)

( * ) Notice: Subject to any disclaimer, the term of this patent is extended or adjusted under 35 U.S.C. 154(b) by 740 days.

This patent is subject to a terminal disclaimer.

(21) Appl. No.: 11/661,391

(22) PCT Filed: Sep. 23, 2005

(86) PCT No.: PCT/KR2005/003174

§ 371 (c)(1),
(2), (4) Date: Feb. 28, 2007

(87) PCT Pub. No.: WO2006/080641

PCT Pub. Date: Aug. 3, 2006

(65) Prior Publication Data

US 2007/0262706 A1    Nov. 15, 2007

(30) Foreign Application Priority Data

Sep. 24, 2004  (KR) ............... 10-2004-0077245

(51) Int. Cl.
*H01L 51/54* (2006.01)
(52) U.S. Cl. ............ 428/690; 428/917; 313/504; 313/506; 252/301.16; 257/40; 257/E51.032; 556/408; 546/15; 546/16; 546/18
(58) Field of Classification Search ............. 556/408
See application file for complete search history.

(56) References Cited

U.S. PATENT DOCUMENTS

| 6,605,373 | B2 | 8/2003 | Woo et al. |
| 6,613,454 | B2 | 9/2003 | Ara et al. |
| 6,630,254 | B2 | 10/2003 | Leclerc et al. |
| 2004/0219386 | A1 | 11/2004 | Thoms |

FOREIGN PATENT DOCUMENTS

| EP | 1 310 539 B1 | 3/2005 |
| JP | 2008-510800 | 4/2008 |
| JP | 2008-511158 | 4/2008 |
| JP | 2008-511159 | 4/2008 |
| JP | 2008-511160 | 4/2008 |
| WO | WO 93/09074 | 5/1993 |
| WO | WO 2006/080640 | 8/2006 |
| WO | WO 2006/080641 | 8/2006 |
| WO | WO 2006/080642 | 8/2006 |
| WO | WO 2006/080643 | 8/2006 |
| WO | WO 2006/080644 | 8/2006 |

OTHER PUBLICATIONS

Tritschler, Wolfgang et al., "Synthese and Konformation von Spiroacridanen", Chem. Ber. 117, 2703-2713 (1984).
Patrick Keller, "Photo-Cross-Linkable Liquid-Crystalline Side-Chain Polysiloxanes", Chemistry of Materials, vol. 2, pp. 3-4, 1990.
Geselowitz et al., "Quantitation of Triple-Helix Formation Using a Photo-Cross-Linkable Aryl Azide/Biotin/Oligonucleotide Conjugate", Bioconjugate Chem., vol. 6, pp. 502-506, 1995.

*Primary Examiner*—D. Lawrence Tarazano
*Assistant Examiner*—Michael Wilson
(74) *Attorney, Agent, or Firm*—McKenna Long & Aldridge LLP

(57) ABSTRACT

Disclosed is an organic light emitting device. The organic light emitting device comprises a first electrode, organic material layer(s) comprising a light emitting layer, and a second electrode. The first electrode, the organic material layer(s), and the second electrode form layered structure and at least one layer of the organic material layer(s) include the compound of Formula 1 or the compound of Formula 1 into which a thermosetting or photo-crosslinkable functional group is introduced.

8 Claims, 1 Drawing Sheet

COMPOUND AND ORGANIC LIGHT EMITTING DEVICE USING THE SAME

This application claims priority to International application No. PCT/KR2005/003174 filed on Sep. 23, 2005, and Korean Application No. 10-2004-0077245 filed on Sep. 24, 2004, both of which are incorporated by reference, as if fully set forth herein.

TECHNICAL FIELD

The present invention relates to an organic light emitting device which comprises a fluorene derivative capable of significantly improving a lifespan, efficiency, and electrochemical and thermal stabilities thereof.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic light emitting device including an organic material having the above-mentioned requirements in the art.

DISCLOSURE OF INVENTION

Technical Problem

Therefore, the object of the present inventions is to provide an organic light emitting device which is capable of satisfying conditions required of a material usable for an organic light emitting device, for example, a proper energy level, electrochemical stability, and thermal stability, and which includes a fluorene derivative having a chemical structure capable of playing various roles required in the organic light emitting device, depending on a substituent group.

Technical Solution

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

[Formula 1]

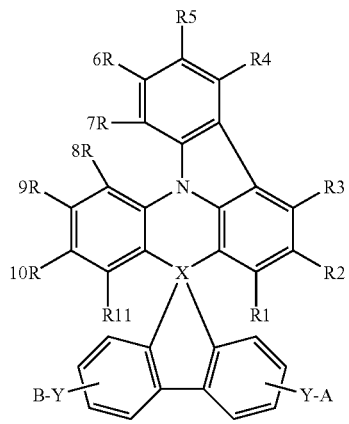

In Formula 1, X is C or Si, A is NZ1Z2, and B is NZ3Z4.
Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups.

Z1 to Z4 are each independently hydrogen; aliphatic hydrocarbons having a carbon number of 1-20; aromatic hydrocarbons; aromatic hydrocarbons which are substituted with at least one substituent group selected from the group consisting of the nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of the nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons.

R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group. They may form aliphatic or hetero condensation rings along with adjacent groups.

R7 and R8 may be directly connected to each other, or may form a condensation ring along with a group selected from the group consisting of O, S, NR, PR, C=O, CRR', and SiRR'. R and R' are each independently or collectively hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound.

A detailed description will be given of the substituent groups of Formula 1.

In Z1 to Z4 as the substituent groups of Formula 1, the aromatic hydrocarbons are exemplified by monocyclic aromatic rings, such as phenyl, biphenyl, and terphenyl, and multicyclic aromatic rings, such as naphthyl, anthracenyl, pyrenyl, and perylenyl. The heterocyclic group is exemplified by thiophene, furan, pyrrole, imidazole, thiazole, oxazole, oxadiazole, thiadiazole, triazole, pyridyl, pyridazyl, pyrazine, quinoline, and isoquinoline.

Examples of aliphatic hydrocarbons having a carbon number of 1-20 include straight chain aliphatic hydrocarbons, branched chain aliphatic hydrocarbons, saturated aliphatic hydrocarbons, and unsaturated aliphatic hydrocarbons. They are exemplified by an alkyl group, such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond, such as styryl; and an alkynyl group having a triple bond, such as an acetylene group.

The carbon number of the alkyl, alkoxy, and alkenyl groups of R1 to R11 of Formula 1 is not limited, but is preferably 1-20.

The length of the alkyl group contained in the compound does not affect the conjugate length of the compound, but may affect the method of applying the compound to the organic light emitting device, for example, a vacuum deposition method or a solution coating method.

Illustrative, but non-limiting, examples of the aryl group of R1 to R11 of Formula 1 include monocyclic aromatic lings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R11 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R11 of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

In addition, illustrative, but non-limiting, examples of the alkenyl, aryl, arylamine, and heterocyclic groups of R1 to R11 of Formula 1 include groups shown in the following Formulae.

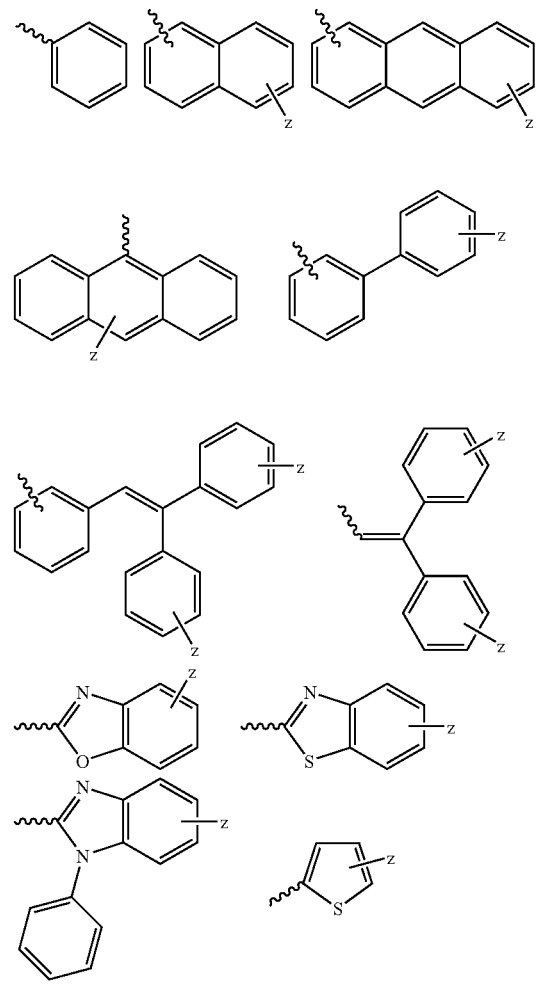

-continued

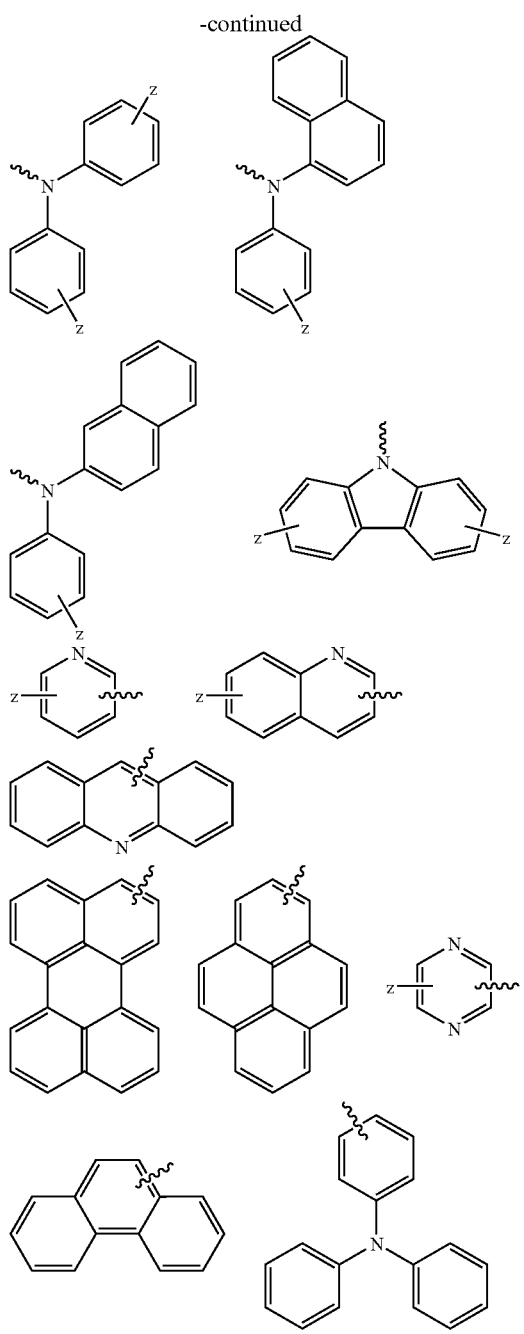

In the above Formulae, Z is a group selected from the group consisting of hydrogen, aliphatic hydrocarbons having a carbon number of 1-20, an alkoxy group, an arylamine group, an aryl group, a heterocyclic group, a nitrile group, and an acetylene group. Examples of the arylamine, aryl, and heterocyclic groups of Z are as shown in the above-mentioned substituent groups of R1 to R11.

According to a preferred embodiment of the present invention, X of Formula 1 is C, and R7 and R8 are directly connected to each other or form a condensation ring along with a group selected from the group consisting of O, S, NR, PR, C=O, CRR', and SiRR' (R and R' are as defined in Formula 1).

According to another preferred embodiment of the present invention, X of Formula 1 is Si, and R7 and R8 are directly connected to each other or form a condensation ring along with a group selected from the group consisting of O, S, NR, PR, C=O, CRR', and SiRR' (R and R' are as defined in Formula 1).

According to still another preferred embodiment of the present invention, the compound of Formula 1 is any one of the compounds of Formulae 2 to 5.

[Formula 2]

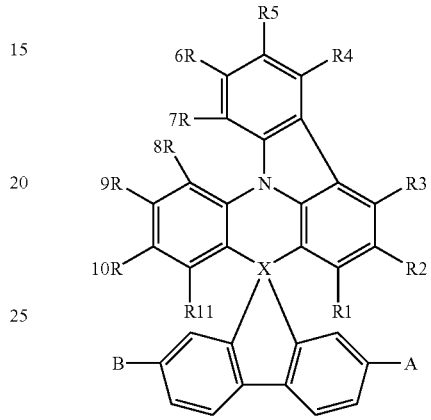

[Formula 3]

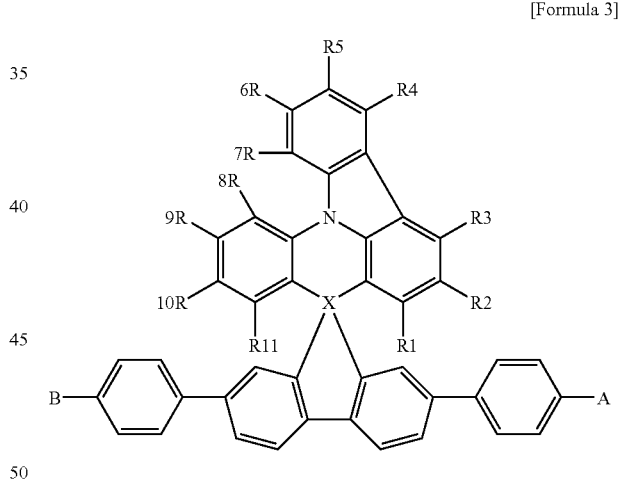

[Formula 4]

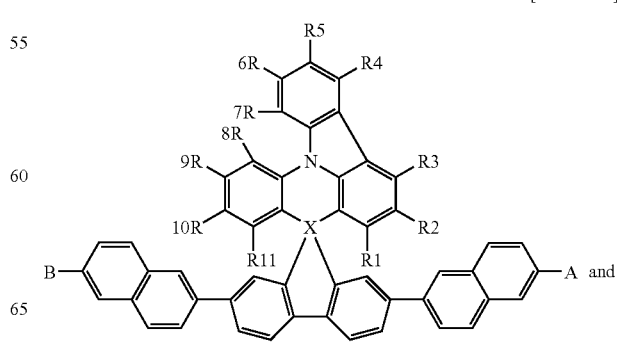

[Formula 5]

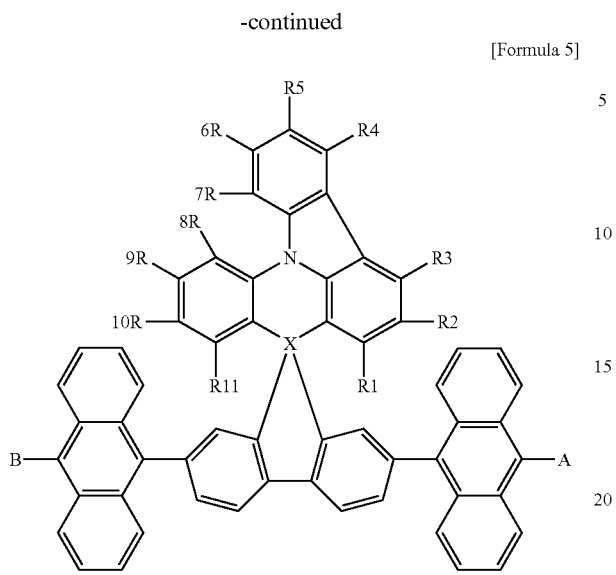

in the Formulae 2 to 5, A and B are as defined in claim 1.

Illustrative, but non-limiting, examples of A and B are as follows. Combination of the compounds of Formulae 2 to 5 and the following groups can form various derivative compounds. For example, if the compound of Formula 2 is combined with the group 1 of the A and B groups, the resulting product will be designated by the compound of Formula 2-1.

[A and B groups]

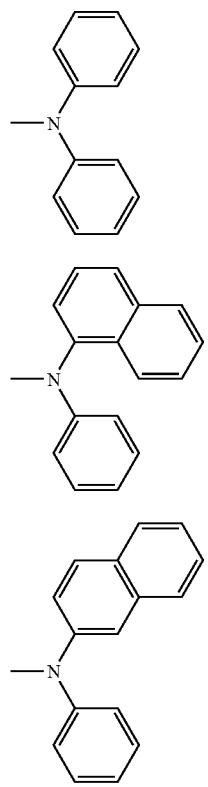

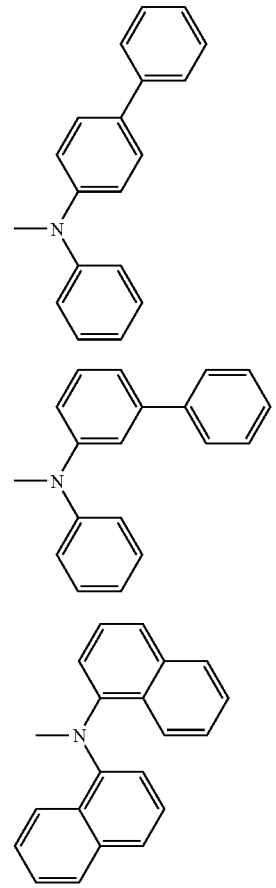

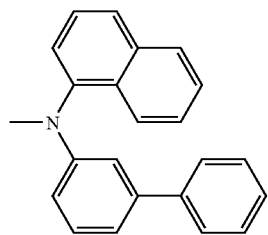
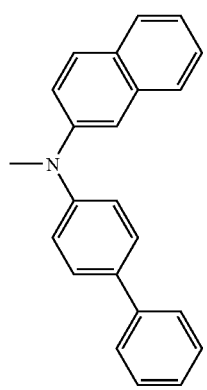
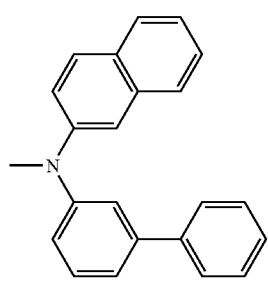
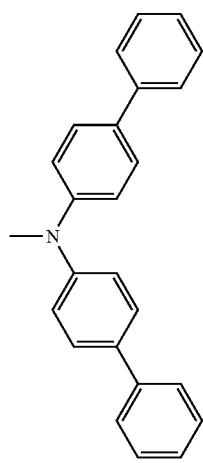
9
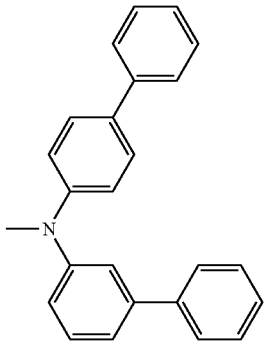
10
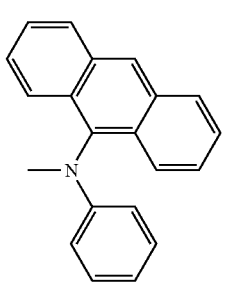
11
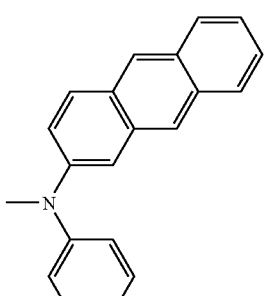
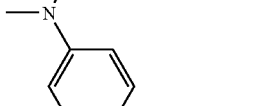
12
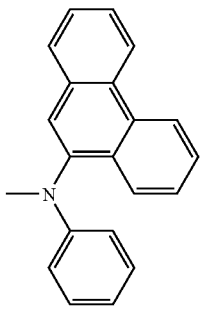
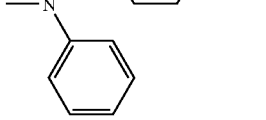
13
14
15
16
17
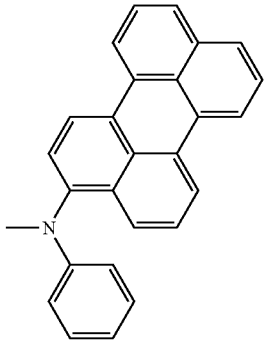

-continued
18
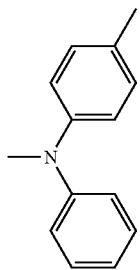
19
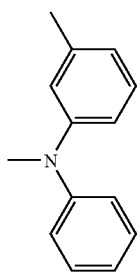
20
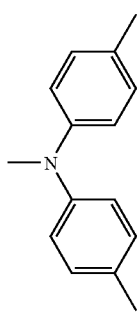
21
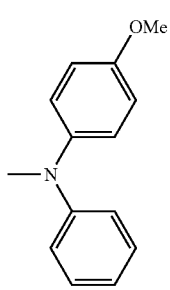
22
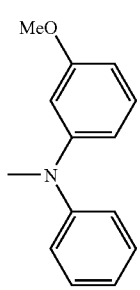
-continued
23
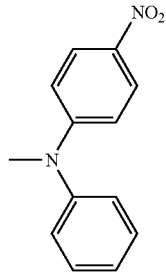
24
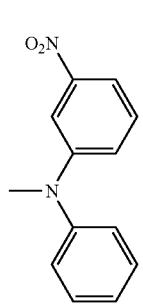
25
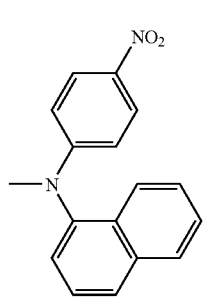
26
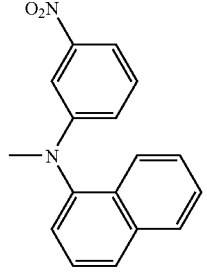
27
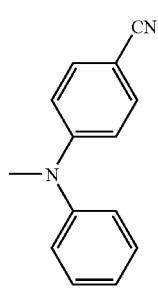

-continued
28
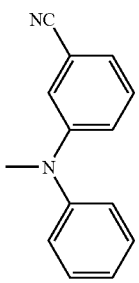
29
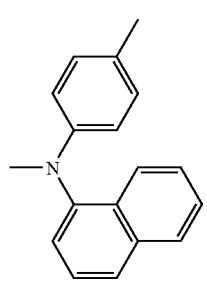
30
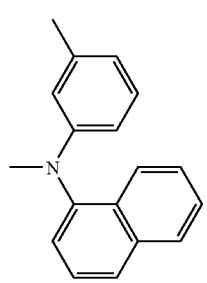
31
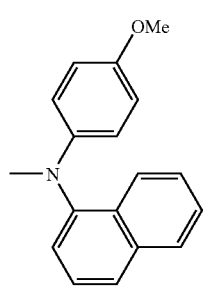
32
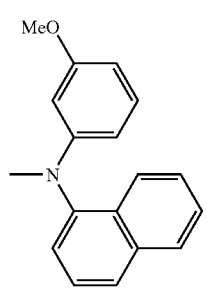
-continued
33
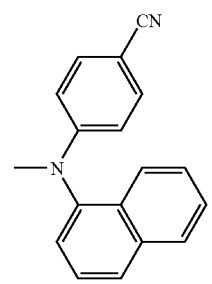
34
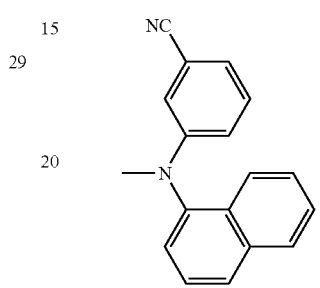
35
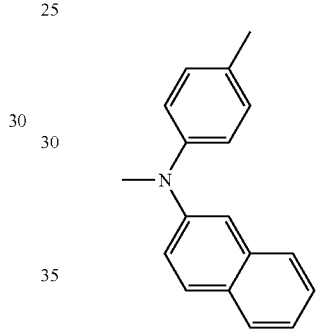
36
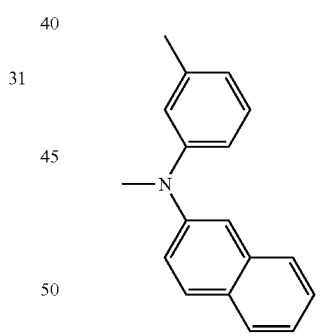
37
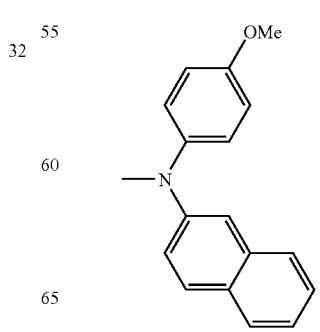

38 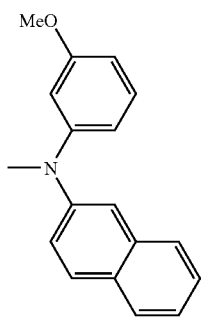
39 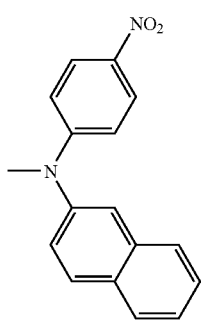
40 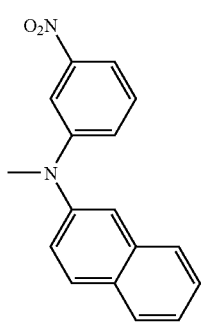
41 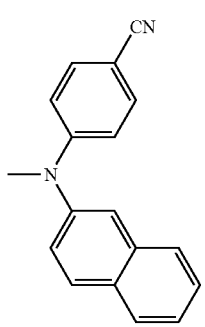
42 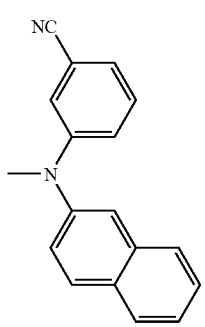
43 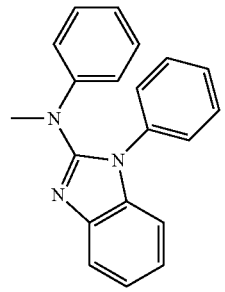
44 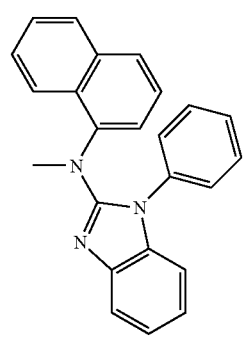
45 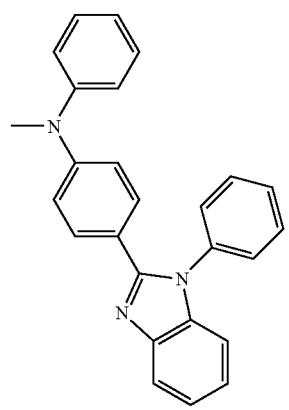
46 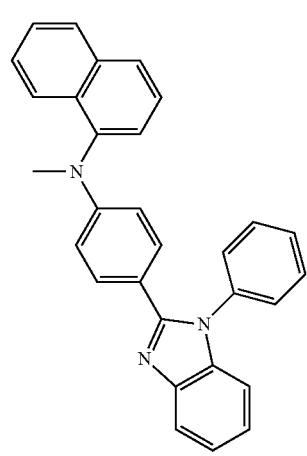

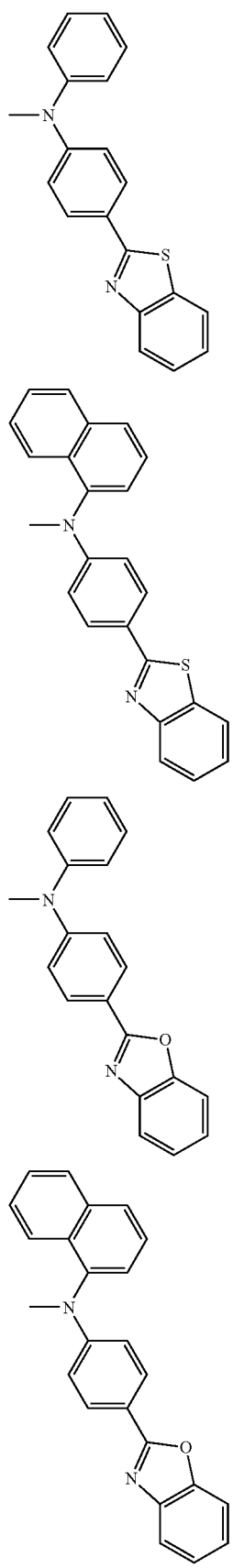
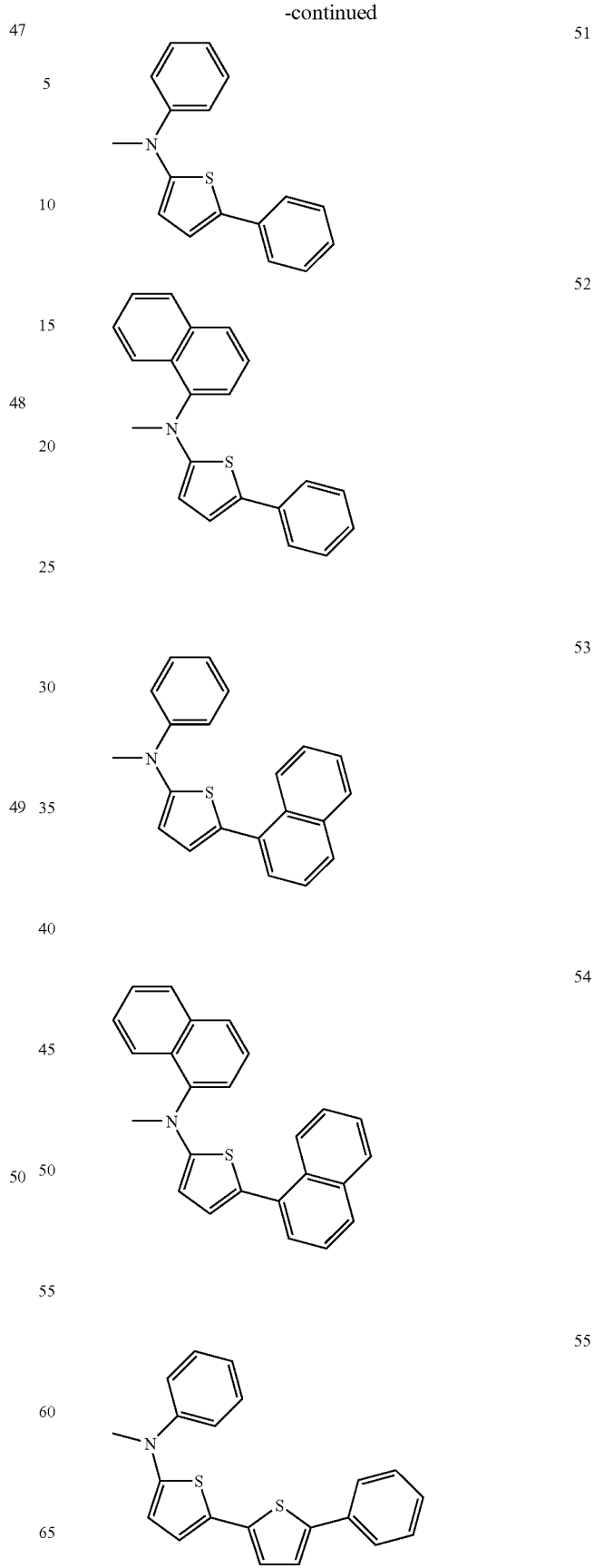

-continued

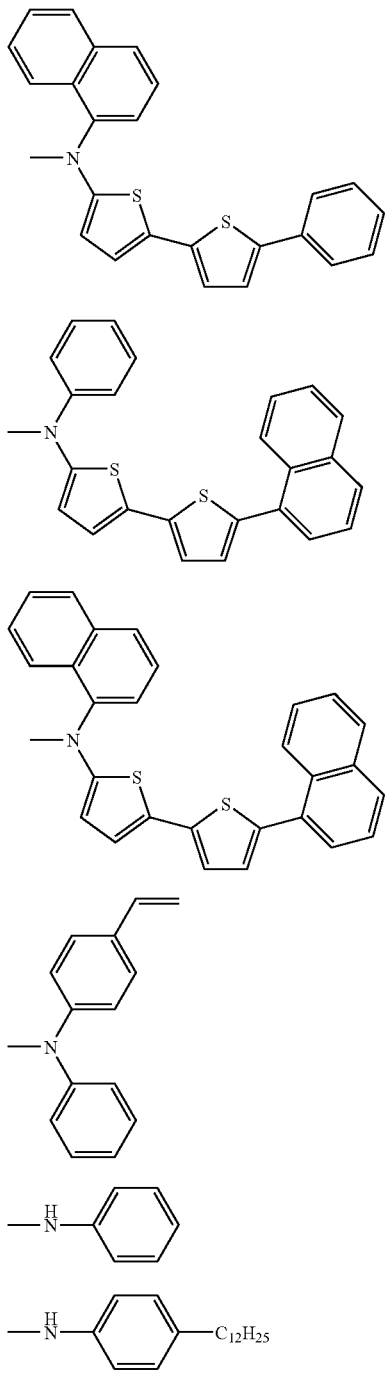

BEST MODE FOR CARRYING OUT THE INVENTION

Figure 1:
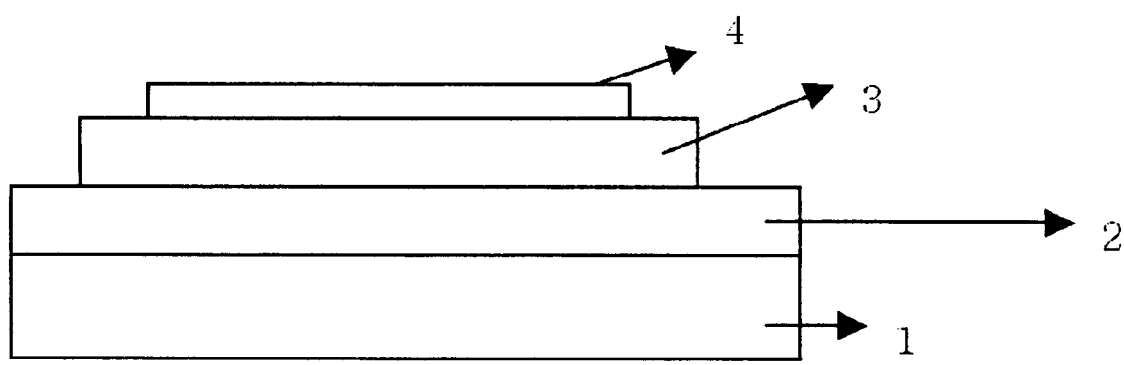
FIG. 1 illustrates an organic light emitting device comprising a substrate 1, an anode 2, a light emitting layer 3, and a cathode 4.
Figure 2:
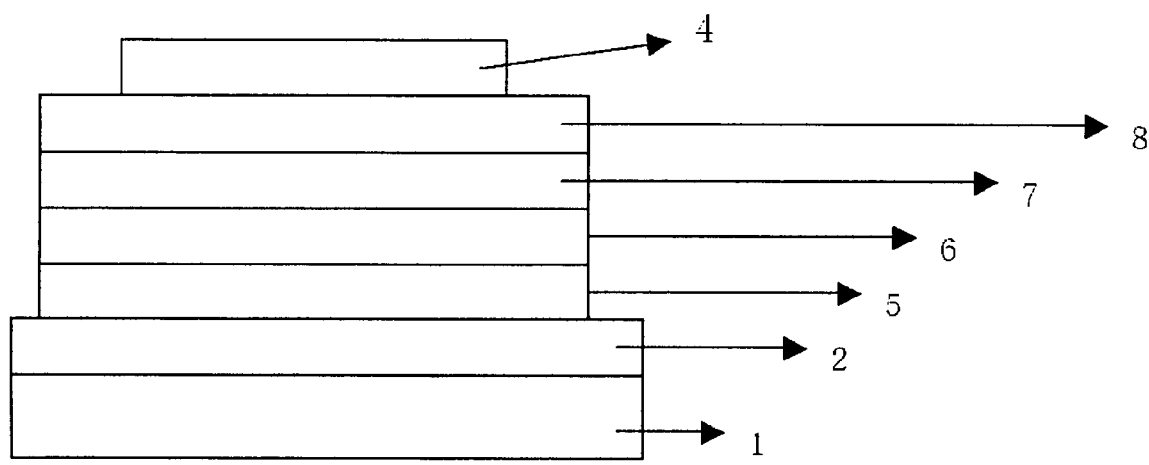
FIG. 2 illustrates an organic light emitting device comprising a substrate 1, an anode 2, a hole injection layer 5, a hole transport layer 6, a light emitting layer 7, an electron transport layer 8, and a cathode 4.

Hereinafter, a detailed description will be given of the present invention.

Various substituent groups are introduced into a core structure shown in Formula 1, in detail, the core structure in which a fluorene group is bonded to a combination of an acridine group and a carbazolyl group to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

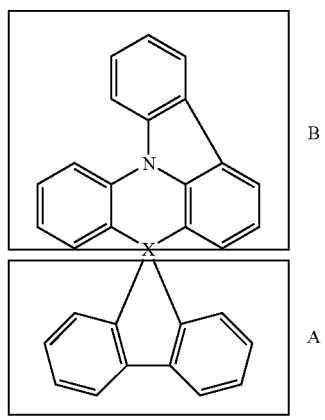

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R11 positions and Z1 to Z4 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO or LUMO energy levels of the compound by introducing various substituent groups into the R1 to R11 and Z1 to Z4 positions of the core structure.

Additionally, by introducing various substituent groups into the core structure, compounds having intrinsic characteristics of the substituent groups can be synthesized. For example, substituent groups, which are frequently applied to hole injection layer materials, hole transport layer materials, light emitting layer materials, and electron transport layer materials which are used during the production of the organic light emitting device, are introduced into the core structure so as to produce substances capable of satisfying requirements of each organic material layer. For example, since the core structure of the compound of Formula 1 includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are symmetrically introduced into the core structure (the A and B portions are located at both sides of the core structure) so as to precisely control the energy band gap, improve interfacial characteristics with organic materials, and apply the compound to various fields.

As well, if the numbers of nitrogen contained in the substituent groups A and B are each set to 1 (if Z1 to Z4 are hetero aromatic amine compounds, the number of nitrogen contained in them is not counted), it is possible to precisely control the HOMO and LUMO energy levels and the energy band gap, and on the other hand interfacial characteristics with the organic materials is improved and thereby make it possible to apply the compound to various fields.

Additionally, various substituent groups are introduced into the steric structure of the compound of Formula 1 using spiro bonding to control the three-dimensional structure of the organic material so as to minimize $\pi$-$\pi$ interaction in the organic material, thereby formation of excimers is prevented.

With respect to the energy band gap and the energy level, for example, since the compound of Formula 2-1, in which arylamine is introduced into the hole transport material or the hole injection material of the structure of Formula 1, has HOMO of 5.37 eV, it has an energy level suitable for the hole injection layer or the hole transport layer. Meanwhile, the compound of Formula 2-1 has the band gap of 3.09 eV, which is still larger than that of NPB, typically used as the hole transport layer material, thus it has a LUMO value of about 2.28 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting device so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2-1, oxidation repeatedly occurs at the same voltage and the current amount is constant. This means that the compound has excellent stability to oxidation.

Meanwhile, since the compound of Formula 1 has a high glass transition temperature (Tg), it has excellent thermal stability. For example, the glass transition temperature of the compound of Formula 2-1 is 131° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 2-1 has excellent solubility to a polar solvent, such as xylene, dichloroethane, or NMP, which is used during the production of the device, and forms a thin film very well through the process using a solution, thus the solution coating process may be applied to produce the device. Additionally, a light emitting wavelength of a thin film or a solid formed using the solution coating process is typically shifted to a longer wavelength due to interaction between molecules, in comparison with a light emitting wavelength in a solution state. Little shift in the wavelength occurs in the compound having the structure shown in Formula 1.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, for example, the compound of Formula 2-61, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the production of the organic light emitting device, forming the organic thin film using the solution coating process, and curing the resulting film, is disclosed in US Pat. No. 2003-0044518 and EP Pat. No. 1146574 A2.

The above documents state that, if the organic material layer is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or acryl group.

The organic light emitting device of the present invention can be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which two or more organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

Mode for the Invention

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, any one of the compounds of the following Formulae, a to c, may be used as a starting material.

[Formula a]

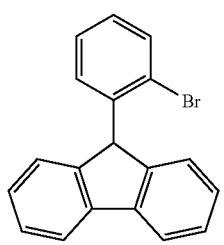

[Formula b]

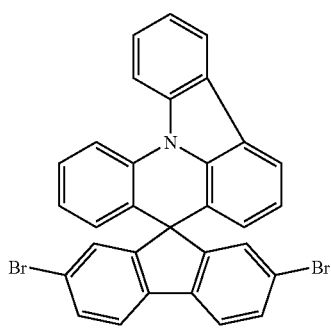

[Formula c]

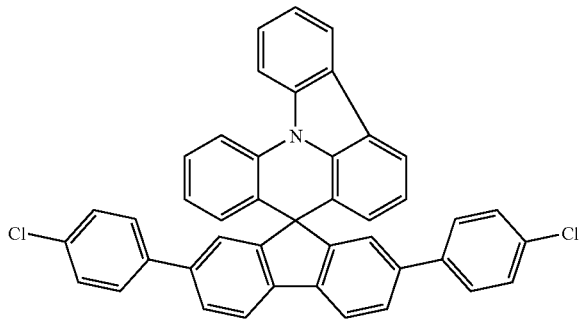

PREPARATION EXAMPLE 1

Preparation of a Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature was conducted, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the resulting white solid compound (800 mg, 25% yield). MS: $[M+H]^+=323$.

PREPARATION EXAMPLE 2

Preparation of a Starting Material Represented by Formula b

The starting material represented by Formula a (6.96 g, 21.6 mmol) was dissolved in 300 ml of purified THF and cooled to $-78°$ C., and n-BuLi (2.5 M in hexane, 8.64 ml, 21.6 mmol) was slowly dropped thereon. Stirring was conducted at the same temperature for 30 min, and 2,7-dibromo-9-fluorenone (6.08 g, 18.0 mmol) was added thereto. After stirring was conducted at the same temperature for 40 min, the temperature was raised to normal temperature and stirring was carried out for an additional 3 hours. The reaction was completed in an ammonium chloride ($NH_4Cl$) aqueous solution, and extraction was conducted with ethyl ether. Water was removed from an organic material layer using anhydrous magnesium sulfate ($MgSO_4$), and an organic solvent was then removed therefrom. The produced solid was dispersed in ethanol, stirred for one day, filtered, and vacuum dried to produce 10.12 g of intermediate material (96.7% yield). The intermediate solid was dispersed in 10 ml of acetic acid, ten drops of concentrated sulfuric acid were added thereto, and reflux was conducted for 4 hours. The resulting solid was filtered, washed with ethanol, and vacuum dried to produce 9.49 g of compound of Formula b (96.8% yield). MS: [M+H]+=563.

PREPARATION EXAMPLE 3

Preparation of a Starting Material Represented by Formula c

The starting material represented by Formula b (10.0 g, 17.8 mmol) was completely dissolved in 200 ml of THF, 4-chloro-phenylboronic acid (8.30 g, 53.3 mmol), 2M potassium carbonate solution, tetrakis(triphenylphosphine)palladium(0) (0.62 g, 0.53 mmol), and 10 ml of ethanol were added thereto, and reflux was conducted for 24 hours. After the reaction was completed, cooling to normal temperature was conducted, and filtration was conducted. Washing was conducted with water and ethanol several times. Recrystallization was conducted with ethanol, and vacuum drying was conducted to produce a compound (9.5 g, 85% yield). MS: $[M+H]^+=625$.

EXAMPLE 1

Preparation of the Compound Represented by Formula 2-1

After the compound of Formula b (3.0 g, 5.3 mmol) was dispersed in 50 ml of xylene, diphenylamine (2.07 g, 12.2 mmol), sodium tert-butoxide (0.074 g, 0.370 mmol), tris(dibenzylideneacetone)dipalladium(0) $(Pd_2(dba)_3$, 0.14 g, 0.25 mmol), and tri-t-butylphosphine (3.50 g, 36.7 mmol) were sequentially added thereto, and reflux was conducted at 120° C. for 2 hours. After cooling to normal temperature was conducted, water was added thereto, a layer separation process was conducted, and water and the solvent were removed from an organic layer. The resulting substance was dispersed in ethyl acetate, and stirred for one day. The solid was filtered and vacuum dried. The resulting solid was subjected to a column separation process using n-hexane/tetrahydrofuran (n-hexane/THF=4/1), and the product was dispersed in ethanol, boiled therein, stirred, and filtered to produce 1.7 g of compound of Formula 2-1 (43% yield). MS: $[M+H]^+=740$.

EXAMPLE 2

Preparation of the Compound Represented by Formula 2-2

After the compound of Formula b (1.13 g, 2.00 mmol) was dispersed in 20 ml of xylene, N-phenyl-1-naphthylamine (0.965 g, 4.40 mmol), sodium tert-butoxide (0.433 g, 4.50 mmol), tris(dibenzylideneacetone)dipalladium(0) $(Pd_2(dba)_3$, 0.073 g, 0.080 mmol), and 50 wt % tri-t-butylphosphine (0.024 g, 0.120 mmol) were sequentially added thereto, and reflux was conducted at 120° C. for 1.5 hours. After cooling to normal temperature was conducted, water was added thereto, a layer separation process was conducted, and water and the solvent were removed from an organic layer. The resulting substance was dispersed in ethyl acetate, and stirred for one day. The solid was filtered and vacuum dried. The resulting solid was subjected to a column separation process using n-hexane/tetrahydrofuran (n-hexane/THF=4/1), and the product was dispersed in ethanol, boiled therein, stirred, and filtered to produce 0.680 g of compound of Formula 2-2 (40.5% yield). MS: $[M+H]^+=841$.

EXAMPLE 3

Preparation of the Compound Represented by Formula 2-3

The compound of Formula b (2.5 g, 4.4 mmol) and N-phenyl-2-naphthylamine (2.2 g, 10 mmol) were dissolved in 50 ml of toluene, sodium-tert-butoxide (1.26 g, 13.2 mmol), tris(dibenzylidene acetone)dipalladium(0) $(Pd_2(dba)_3$, 0.08 g, 0.08 mmol), and 50 wt % tri-tert-butylphosphine (0.02 g, 0.13 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 2-3 (1.92 g, yield 52%). MS: $[M+H]^+=839$.

EXAMPLE 4

Preparation of the Compound Represented by Formula 2-4

1) Synthesis of arylamine (N-phenyl-4-biphenylamine) to produce the compound represented by Formula 2-4: aniline (10 ml, 109.74 mmol) and 4-bromobiphenylamine (25.6 g, 109.7 mmol) were dissolved in 300 ml of toluene, and bis(dibenzylidene acetone)palladium(0) $(Pd(dba)_2$, 1.26 g, 2.20 mmol), 50 wt % tri-tert-butylphosphine toluene solution (1.30 ml, 3.29 mmol), and sodium-tert-butoxide (21.09 g, 219.5 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=10/1), stirring was conducted using petroleum ether, and vacuum drying was conducted to produce arylamine (15 g, yield 56%). MS: $[M+H]^+=246$.

2) The compound of Formula b (2.5 g, 4.44 mmol) and N-phenyl-4-biphenylamine (2.72 g, 11.1 mmol) were dissolved in 30 ml of toluene, and bis(dibenzylidene acetone)palladium(0) (Pd(dba), 0.051 g, 0.09 mmol), 50 wt % tri-tert-butylphosphine toluene solution (0.05 ml, 0.13 mmol), and sodium-tert-butoxide (1.707 g, 17.76 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=10/1), stirring was conducted using petroleum ether, and vacuum drying was conducted to produce the compound of Formula 2-4 (3.2 g, yield 80.8%). MS: $[M+H]^+=893$.

EXAMPLE 5

Preparation of the Compound Represented by Formula 2-6

1) Synthesis of arylamine (1,1-dinaphthylamine) to produce the compound represented by Formula 2-6: 1-aminonaphthalene (10.0 g, 69.84 mmol) and 1-bromonaphthalene (7.47 ml, 53.7 mmol) were dissolved in 200 ml of toluene, and tris(dibenzylidene acetone)dipalladium(0) (Pd$_2$(dba)$_3$, 1.21 g, 2.10 mmol), 50 wt % tri-tert-butylphosphine (1.38 ml, 2.79 mmol), and sodium-tert-butoxide (16.78 g, 174.6 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce arylamine (5.26 g, yield 28%). MS: [M+H]$^+$=270.

2) The compound of Formula b (5.0 g, 8.88 mmol) and 1,1-dinaphthylamine (5.26 g, 19.5 mmol) were dissolved in 50 ml of toluene, and bis(dibenzylidene acetone)palladium (0) (Pd(dba)$_2$, 0.204 g, 0.36 mmol), 50 wt % tri-tert-butylphosphine toluene solution (0.31 ml, 0.62 mmol), and sodium-tert-butoxide (4.694 g, 48.84 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 2-6 (3.29 g, yield 39.4%). MS: [M+H]$^+$=941.

EXAMPLE 6

Preparation of the Compound Represented by Formula 2-8

1) Synthesis of arylamine (1,4-naphthylbiphenylamine) to produce the compound represented by Formula 2-8: 1-aminonaphthalene (7.4 g, 51.48 mmol) and 4-bromobiphenyl (12 g, 51.48 mmol) were dissolved in 200 ml of toluene, and bis(dibenzylidene acetone)palladium(0) (Pd(dba)$_2$, 0.89 g, 1.54 mmol), 50 wt % tri-tert-butylphosphine (0.60 ml, 1.54 mmol), and sodium-tert-butoxide (9.90 g, 103.0 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce arylamine (6.3 g, yield 42%). MS: [M+H]$^+$=295.

2) The compound of Formula b (3 g, 5.33 mmol) and 1,4-naphthylbiphenylamine (3.62 g, 12.25 mmol) were dissolved in 80 ml of toluene, and bis(dibenzylidene acetone)palladium(0) (Pd(dba)$_2$, 0.06 g, 0.11 mmol), 50 wt % tri-tert-butylphosphine toluene solution (0.06 ml, 0.16 mmol), and sodium-tert-butoxide (1.54 g, 16.0 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 2-8 (3.2 g, yield 61%). MS: [M+H]$^+$=992.

EXAMPLE 7

Preparation of the Compound Represented by Formula 2-12

1) Synthesis of arylamine (4,4-dibiphenylamine) to produce the compound represented by Formula 2-12: 4-aminobiphenyl (30.5 g, 180.17 mmol) and 4-bromobiphenyl (40 g, 171.59 mmol) were dissolved in 500 ml of toluene, and bis(dibenzylidene acetone)palladium(0) (Pd(dba)$_2$, 2.07 g, 3.60 mmol), 50 wt % tri-tert-butylphosphine (2.2 ml, 5.41 mmol), and sodium-tert-butoxide (51.94 g, 540.5 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce 4,4-dibiphenylamine (32 g, yield 58%). MS: [M+H]$^+$=321.

2) The compound of Formula b (5.4 g, 0.62 mmol) and 4,4-dibiphenylamine (6.80 g, 2.12 mmol) were dissolved in 200 ml of toluene, and bis(dibenzylidene acetone)palladium (0) (Pd(dba)$_2$, 0.243 g, 0.423 mmol), 50 wt % tri-tert-butylphosphine toluene solution (0.260 ml, 0.635 mmol), and sodium-tert-butoxide (6.10 g, 63.5 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran (n-hexane/THF=9/1), stirring was conducted using petroleum ether, and vacuum drying was conducted to produce the compound of Formula 2-12 (6.3 g, yield 63%). MS: [M+H]$^+$=1044.

EXAMPLE 8

Preparation of the Compound Represented by Formula 2-18

The compound of Formula b (2.5 g, 4.4 mmol) and 4-methyldiphenylamine (2.0 g, 10 mmol) were dissolved in 50 ml of xylene, sodium-tert-butoxide (1.26 g, 13.2 mmol), tris (dibenzylidene acetone)dipalladium(0) (Pd$_2$(dba)$_3$, 0.08 g, 0.08 mmol), and 50 wt % tri-tert-butylphosphine (0.02 g, 0.13 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 2-18 (1.8 g, yield 52%). MS: [M+H]$^+$=768.

EXAMPLE 9

Preparation of the Compound Represented by Formula 2-59

1) The compound of Formula b (2.25 g, 4 mmol) and aniline (0.8 ml, 8.8 mmol) were dissolved in 40 ml of xylene, and tri-tert-butylphosphine (0.05 g, 0.24 mmol) and tris (dibenzylidene acetone)dipalladium(0) (Pd$_2$(dba)$_2$, 0.15 g, 0.16 mmol) were sequentially added thereto. After reflux was conducted for 6 hours, cooling to normal temperature was conducted, and water was added thereto. The organic layer was separated, and a column separation process was conducted using n-hexane and tetrahydrofuran (n-hexane/THF=4/1) to produce 1.23 g of a light brown solid. MS: [M+H]$^+$=588.

2) 0.59 g of the above compound (1 mol), 4-bromostyrene (0.28 ml, 2.1 mmol), sodium-tert-butoxide (0.21 g, 2.2 mmol), tri-tert-butylphosphine (0.012 g, 0.06 mmol), and tris(dibenzylidene acetone)dipalladium(0) (Pd$_2$(dba)$_3$, 0.037 g, 0.04 mmol) were added to xylene, and reflux was conducted for 3 hours. After cooling to normal temperature, water was added thereto, the organic layer was extracted, and a column separation process was conducted using n-hexane and tetrahydrofuran (n-hexane/THF=4/1) to produce the compound of Formula 2-59 (0.2 g). MS: [M+H]$^+$=792.

EXAMPLE 10

Preparation of the Compound Represented by Formula 2-61

The compound of Formula b (1.12 g, 2.0 mmol) and 4-dodecylaniline (0.53 g, 2.0 mmol) were dissolved in distilled toluene (30 ml), sodium-tert-butoxide (0.58 g, 6.0 mmol), tris(dibenzylidene acetone)dipalladium(0) (Pd$_2$(dba)$_3$, 0.046 g, 0.05 mmol), and tri-tert-butylphosphine (0.06 g, 0.3 mmol) were added thereto, and stirring was conducted in a nitrogen atmosphere at 100° C. After 36 hours, ammonia water was added to the reaction solution to complete the reaction, and the organic layer was extracted. The extracted organic layer was concentrated in tetrahydrofuran (THF) and reprecipitated in ethanol. The resulting yellow solid was filtered to separate it, and additional reprecipitation was repeated twice. The filtered yellow solid was dissolved in tetrahydrofuran (THF), and then adsorbed onto a silica gel to achieve column separation. n-hexane and tetrahydrofuran (n-hexane/THF=4/1) were used as a developing solvent to remove developed impurities, and a product mixture was developed with tetrahydrofuran (THF) and thus separated. The separated product mixture was poured on a celite layer (Celite 545) to be filtered, and the filtered solution was concentrated with tetrahydrofuran (THF). The concentrated product was reprecipitated in ethanol, filtered, and vacuum dried to produce a yellow polymer mixture of Formula 2-61 (0.89 g, yield 54%).

MALDI-MS: [M+H]$^+$=3318, 3980, 4644, 5309, 5971, 6634, 7302.

GPC (polystyrene standard)

Mn Mw Mp Mz PDI 10222 19685 22343 31802 1.9

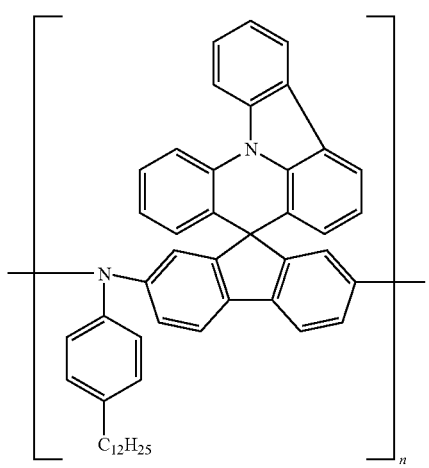

EXAMPLE 11

Preparation of the Compound Represented by Formula 3-1

The compound of Formula c (5.08 g, 8.11 mmol) and diphenylamine (3.02 g, 17.8 mmol) were dissolved in 100 ml of toluene, sodium-tert-butoxide (5.15 g, 53.6 mmol), bis (dibenzylidene acetone)palladium(0) (Pd(dba)$_2$, 0.21 g, 0.36 mmol), and tri-tert-butylphosphine (0.11 ml, 0.54 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 3-1 (4.30 g, yield 54.6%). MS: [M+H]$^+$=891.

EXAMPLE 12

Preparation of the Compound Represented by Formula 3-2

The compound of Formula c (5.0 g, 10.32 mmol) and N-phenyl-1-naphthylamine (3.85 g, 17.56 mmol) were dissolved in 50 ml of toluene, sodium-tert-butoxide (2.3 g, 23.94 mmol), bis(dibenzylidene acetone)palladium(0) (Pd(dba)$_2$, 0.09 g, 0.16 mmol), and tri-tert-butylphosphine (0.12 ml, 0.24 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=4/1), recrystallization was conducted with ethanol, and vacuum drying was conducted to produce the compound of Formula 3-2 (4.8 g, yield 61%). MS: [M+H]$^+$=991.

EXAMPLE 13

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using oxygen plasma for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

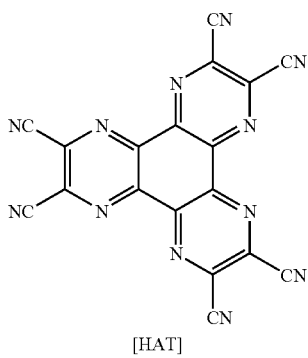

[HAT]

The compound of Formula 2-1 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

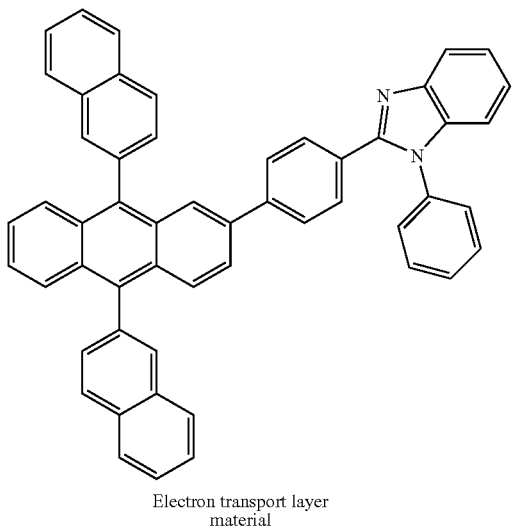

Electron transport layer material

Lithium fluoride (LiF) having a thickness of 12 Å and aluminum having a thickness of 2000 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1\text{-}3\times10^{-7}$.

The resulting device had an electric field of 4.63 V at a forward current density of 100 mA/cm$^2$, and a spectrum having a light efficiency of 1.89 lm/W. The operation and light emission of the device at the above-mentioned actuating voltage mean that the compound of Formula 2-1, which formed the layer between the hole injection layer and the light emitting layer, functions to transport holes.

EXAMPLE 14

Production of an Organic Light Emitting Device

HAT was deposited on an ITO substrate, which was prepared through the procedure of example 13, to a thickness of 80 Å to form a thin film. The thin film can improve the characteristics of the interface of the substrate and a hole injection layer. Subsequently, the compound of Formula 2-1 was deposited on the thin film to a thickness of 800 Å to form the hole injection layer.

NPB was deposited on the hole injection layer to a thickness of 300 Å to form an injection transport layer, and Alq3 was then deposited thereon to a thickness of 300 Å to form a light emitting layer. An electron transport layer and a cathode were formed on the light emitting layer through the same procedure as example 13.

In the present example, deposition speeds of an organic material and the cathode were the same as those of example 13.

The resulting device had an electric field of 5.76 V at a forward current density of 100 mA/cm$^2$, and a spectrum having a light efficiency of 1.93 lm/W. The operation and light emission of the device at the above-mentioned actuating voltage mean that the compound of Formula 2-1, which formed the layer between the thin film on the substrate and the hole transport layer, functions to inject holes.

EXAMPLE 15

Production of an Organic Light Emitting Device

The procedure of example 13 was repeated to produce a device except that the compound of Formula 2-2 was used instead of the compound of Formula 2-1 as a hole transport layer.

The resulting device had an electric field of 4.43 V at a forward current density of 100 mA/cm$^2$, and a spectrum having a light efficiency of 1.81 lm/W. The operation and light emission of the device at the above-mentioned actuating voltage mean that the compound of Formula 2-2, which formed the layer between the hole injection layer and the light emitting layer, functions to transport holes.

EXAMPLE 16

Production of an Organic Light Emitting Device

The procedure of example 14 was repeated to produce a device except that the compound of Formula 2-1 used as a hole injection layer was substituted with the compound of Formula 2-2.

The resulting device had an electric field of 5.30 V at a forward current density of 100 mA/cm$^2$, and a spectrum having a light efficiency of 1.80 lm/W. The operation and light emission of the device at the above-mentioned actuating voltage mean that the compound of Formula 2-2, which formed the layer between the thin film on the substrate and the hole transport layer, functions to inject holes.

EXAMPLE 17

Production of an Organic Light Emitting Device

HAT was deposited on an ITO substrate, which was prepared through the procedure of example 14, to a thickness of 80 Å to form a thin film. Subsequently, the compound of Formula 2-2 was deposited on the thin film to a thickness of 1100 Å to form a layer for injecting and transporting holes.

Alq3 was deposited thereon to a thickness of 300 Å to form a light emitting layer. An electron transport layer and a cathode were formed on the light emitting layer through the same procedure as example 14.

In the present example, deposition speeds of an organic material and the cathode were the same as those of example 14.

The resulting device had an electric field of 5.14 V at a forward current density of 100 mA/cm$^2$, and a spectrum having a light efficiency of 2.10 lm/W.

EXAMPLE 18

Production of an Organic Light Emitting Device

The procedure of example 14 was repeated to produce a device except that the compound of Formula 2-1 used as a hole injection layer was substituted with the compound of Formula 2-3.

The resulting device had an electric field of 5.95 V at a forward current density of 100 mA/cm$^2$, and a spectrum having a light efficiency of 1.77 lm/W.

EXAMPLE 19

Production of an Organic Light Emitting Device

The procedure of example 14 was repeated to produce a device except that the compound of Formula 2-1 used as a hole injection layer was substituted with the compound of Formula 2-4.

The resulting device had an electric field of 6.34 V at a forward current density of 100 mA/cm$^2$, and a spectrum having a light efficiency of 1.74 lm/W.

EXAMPLE 20

Production of an Organic Light Emitting Device

The procedure of example 13 was repeated to produce a device except that the compound of Formula 2-4 was used instead of the compound of Formula 2-1 as a hole transport layer.

The resulting device had an electric field of 7.26 V at a forward current density of 100 mA/cm$^2$, and a spectrum having a light efficiency of 2.0 lm/W.

EXAMPLE 21

Production of an Organic Light Emitting Device

The procedure of example 14 was repeated to produce a device except that the compound of Formula 2-1 used as a hole injection layer was substituted with the compound of Formula 2-6.

The resulting device had an electric field of 6.50 V at a forward current density of 100 mA/cm$^2$, and a spectrum having a light efficiency of 1.90 lm/W.

EXAMPLE 22

Production of an Organic Light Emitting Device

The procedure of example 14 was repeated to produce a device except that the compound of Formula 2-1 used as a hole injection layer was substituted with the compound of Formula 2-8.

The resulting device had an electric field of 5.49 V at a forward current density of 100 mA/cm$^2$, and a spectrum having a light efficiency of 1.73 lm/W.

EXAMPLE 23

Production of an Organic Light Emitting Device

The procedure of example 13 was repeated to produce a device except that the compound of Formula 2-8 was used instead of the compound of Formula 2-1 as a hole transport layer.

The resulting device had an electric field of 7.13 V at a forward current density of 100 mA/cm$^2$, and a spectrum having a light efficiency of 2.08 lm/W.

EXAMPLE 24

Production of an Organic Light Emitting Device

The procedure of example 14 was repeated to produce a device except that the compound of Formula 2-1 used as a hole injection layer was substituted with the compound of Formula 2-12.

The resulting device had an electric field of 7.3 V at a forward current density of 100 mA/cm$^2$, and a spectrum having a light efficiency of 1.75 lm/W.

EXAMPLE 25

Production of an Organic Light Emitting Device

The procedure of example 13 was repeated to produce a device except that the compound of Formula 2-12 was used instead of the compound of Formula 2-1 as a hole transport layer.

The resulting device had an electric field of 7.0 V at a forward current density of 100 mA/cm$^2$, and a spectrum having a light efficiency of 1.82 lm/W.

EXAMPLE 26

Production of an Organic Light Emitting Device

The procedure of example 14 was repeated to produce a device except that the compound of Formula 2-18 was used instead of the compound of Formula 2-1.

The resulting device had an electric field of 6.68 V at a forward current density of 100 mA/cm$^2$, and a spectrum having a light efficiency of 1.7 lm/W.

EXAMPLE 27

Production of an Organic Light Emitting Device

The procedure of example 13 was repeated to produce a device except that the compound of Formula 2-18 was used instead of the compound of Formula 2-1.

The resulting device had an electric field of 6.02 V at a forward current density of 100 mA/cm², and a spectrum having a light efficiency of 1.48 lm/W.

EXAMPLE 28

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted.

A solution, in which the compound of Formula 2-61 was dissolved in chlorobenzene in a concentration of 0.5%, was filtered using a PVDF filter of 0.20 μm, applied on the substrate using a spin coating process at a speed of 2000 rpm for 20 sec, and dried in an argon atmosphere at 120° C. for 5 min to produce a hole injection layer having a thickness of 350 Å.

After the substrate was transported to a vacuum evaporator, Alq3 was deposited thereon to a thickness of 500 Å to form a layer acting both as a light emitting layer and as an electron transport layer.

Lithium fluoride (LiF) having a thickness of 15 Å and aluminum having a thickness of 1500 Å were sequentially deposited on the electron transport layer to form a cathode.

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3\times10^{-7}$.

The resulting device had an electric field of 7.17 V at a forward current density of 100 mA/cm², and a spectrum having a light efficiency of 0.68 lm/W.

EXAMPLE 29

Production of an Organic Light Emitting Device

The procedure of example 13 was repeated to produce a device except that the compound of Formula 2-1 used as a hole transport layer was substituted with the compound of Formula 3-1.

The resulting device had an electric field of 7.30 V at a forward current density of 100 mA/cm², and a spectrum having a light efficiency of 1.75 lm/W.

EXAMPLE 30

Production of an Organic Light Emitting Device

The procedure of example 13 was repeated to produce a device except that the compound of Formula 2-1 used as a hole transport layer was substituted with the compound of Formula 3-2.

The resulting device had an electric field of 7.50 V at a forward current density of 100 mA/cm², and a spectrum having a light efficiency of 1.83 lm/W.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

The invention claimed is:

1. An organic light emitting device, comprising:
a first electrode;
organic material layer(s) comprising a light emitting layer, wherein at least one layer of the organic material layer(s) includes the compound of Formula 1; and
a second electrode; wherein the first electrode, the organic material layer(s), and the second electrode form layered structure,

[Formula 1]

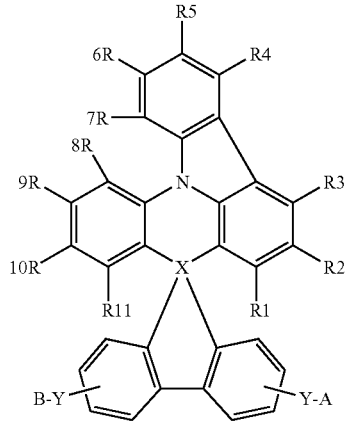

wherein X is C or Si;
A is NZ1Z2;
B is NZ3Z4;
Y is a bond; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups;
Z1 to Z4 are each independently hydrogen; aliphatic hydrocarbons having a carbon number of 1-20; aromatic hydrocarbons; aromatic hydrocarbons which are substituted with at least one substituent group selected from the group consisting of nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of nitro, nitrile, halogen, alkyl, alkoxy, amino, aromatic hydrocarbon, and heterocyclic groups; a thiophenyl group which is substituted with hydrocarbons having a carbon number of 1-20 or aromatic hydrocarbons having a carbon number of 6-20; or a boron group which is substituted with aromatic hydrocarbons;
R1 to R11 are each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group, and R1 to R11 may form aliphatic or hetero condensation rings along with adjacent groups; and R7 and R8 may be directly connected to each other, or may form a condensation ring along with a group selected from the group consisting of O, S, NR, PR, C=O, CRR', and SiRR', wherein R and R' are each independently or collectively are hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound.

2. The organic light emitting device as set forth in claim 1, wherein R7 and R8 of Formula 1 form the condensation ring along with a group selected from the group consisting of O, S, NR, PR, C=O, CRR', and SiRR'.

3. The organic light emitting device as set forth in claim 1, wherein the compound of Formula 1 is any one of compounds of Formulae 2 to 5:

[Formula 2]

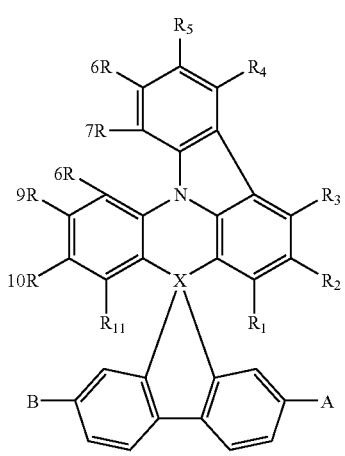

[Formula 3]

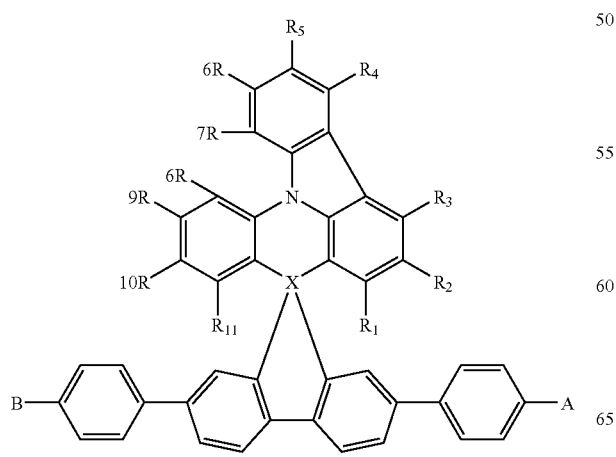

[Formula 4]

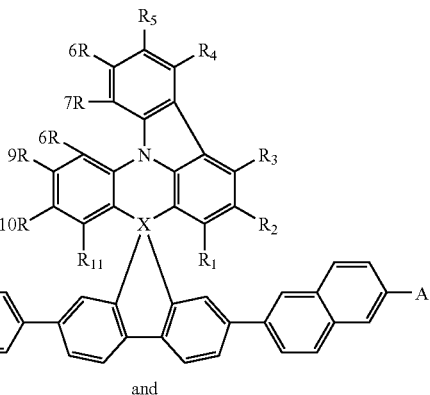

and

[Formula 5]

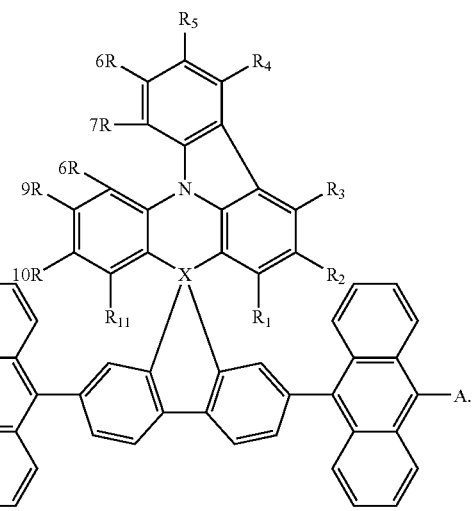

4. The organic light emitting device as set forth in claim 1, wherein A and B of Formula 1 are each independently any one of following groups:

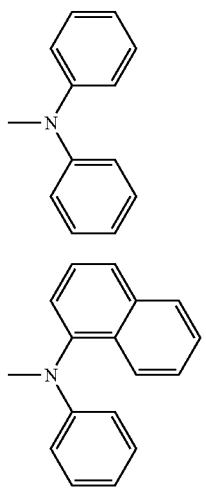

3
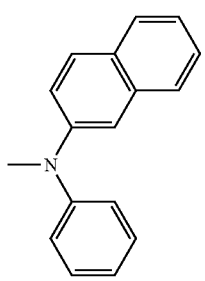
4
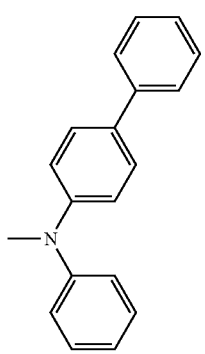
5
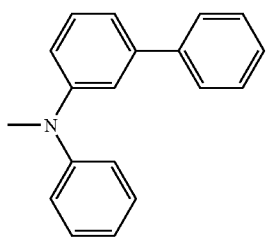
6
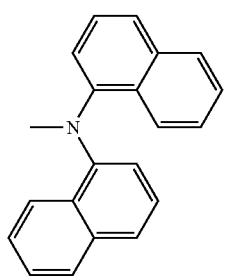
7
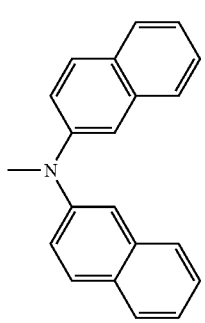
8
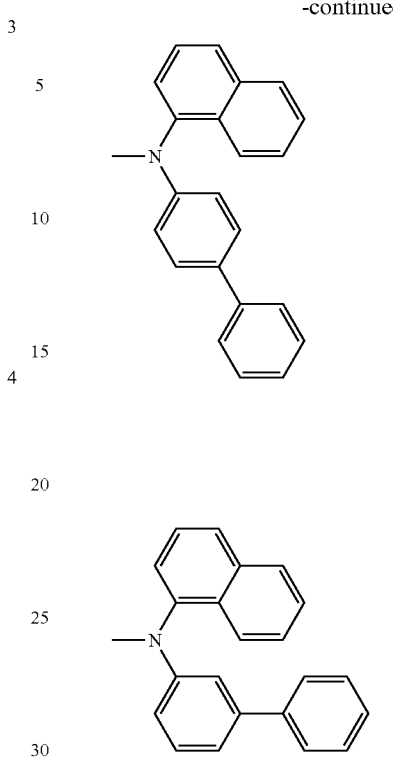
9
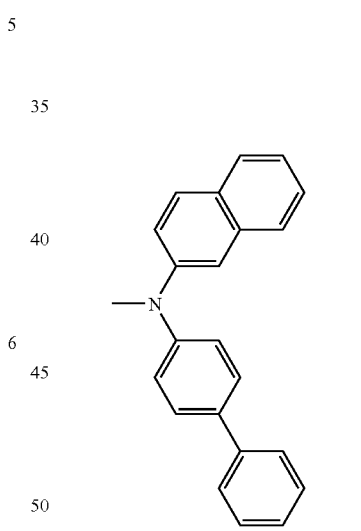
10
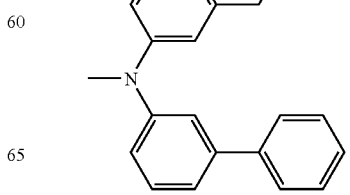
11

-continued
12
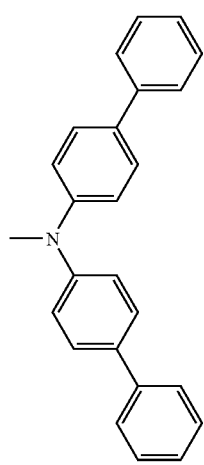
13
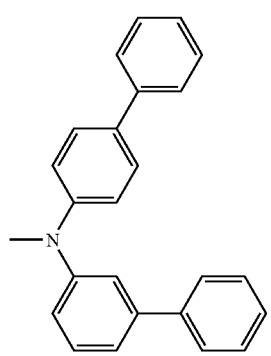
14
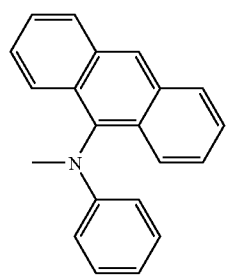
15
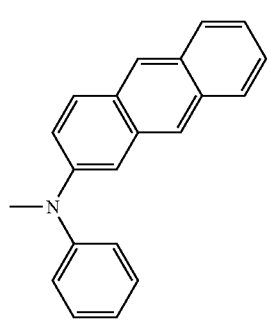
-continued
16
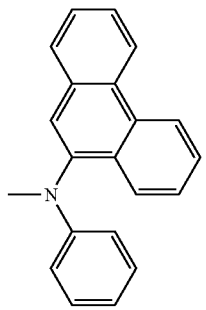
17
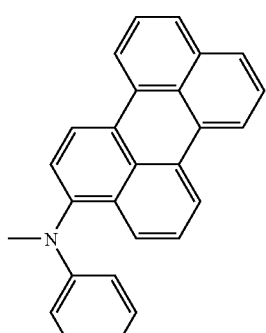
18
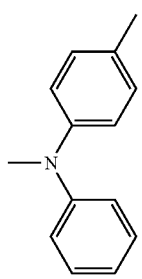
19
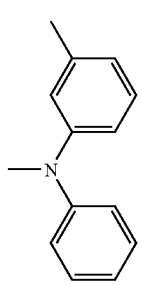
20
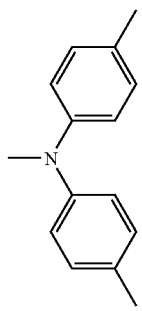

-continued
21
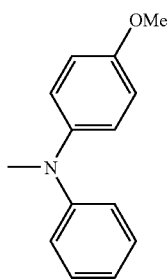
22
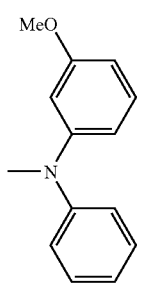
23
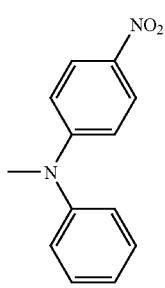
24
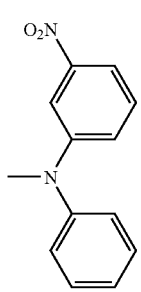
25
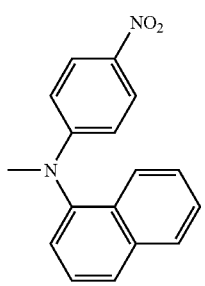
-continued
26
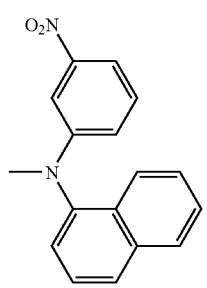
27
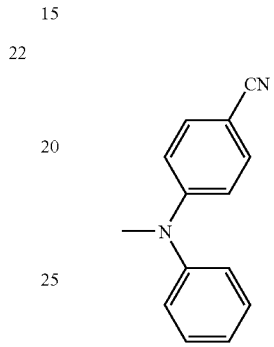
28
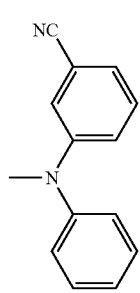
29
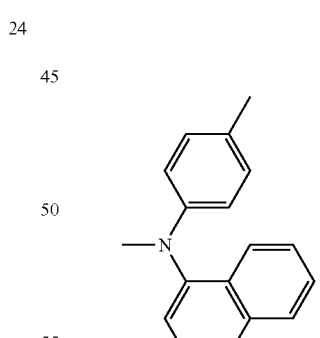
30
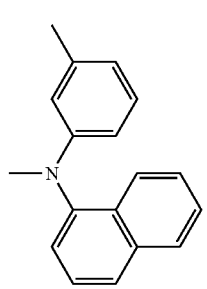

-continued
31
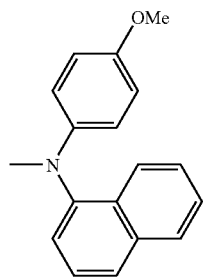
32
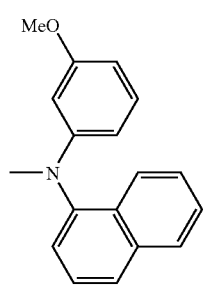
33
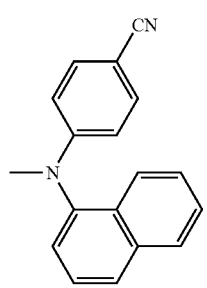
34
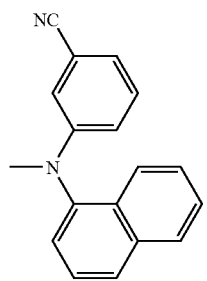
35
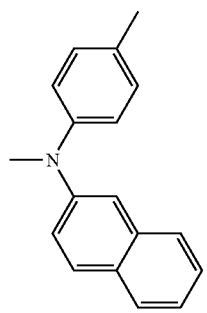
-continued
36
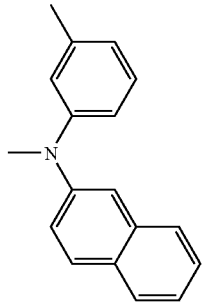
37
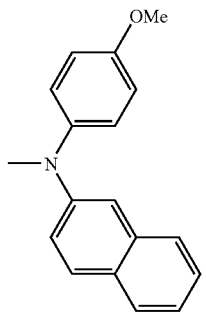
38
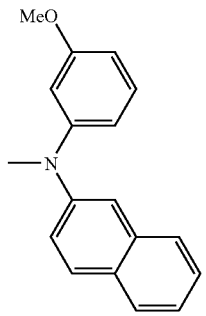
39
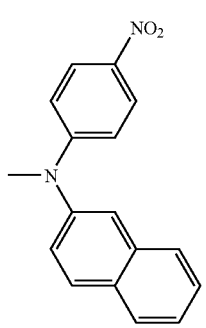
40
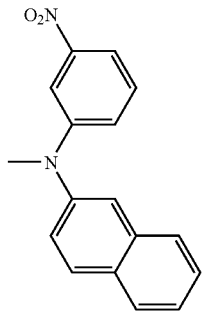

-continued
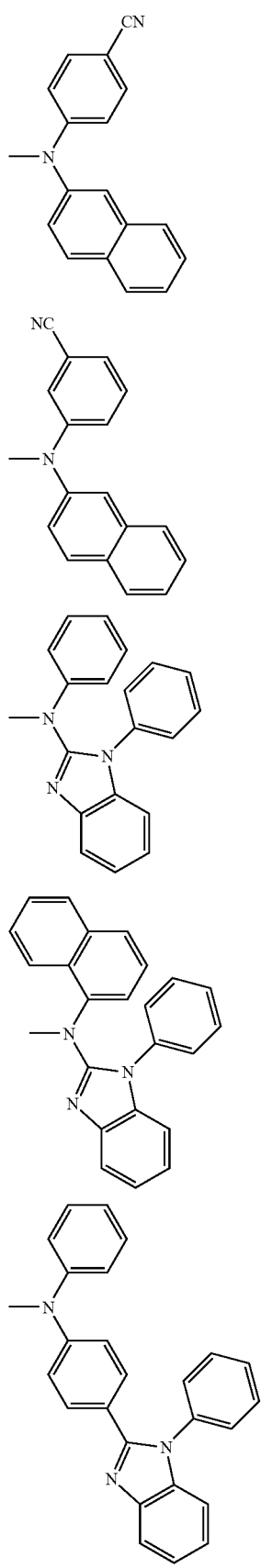
-continued
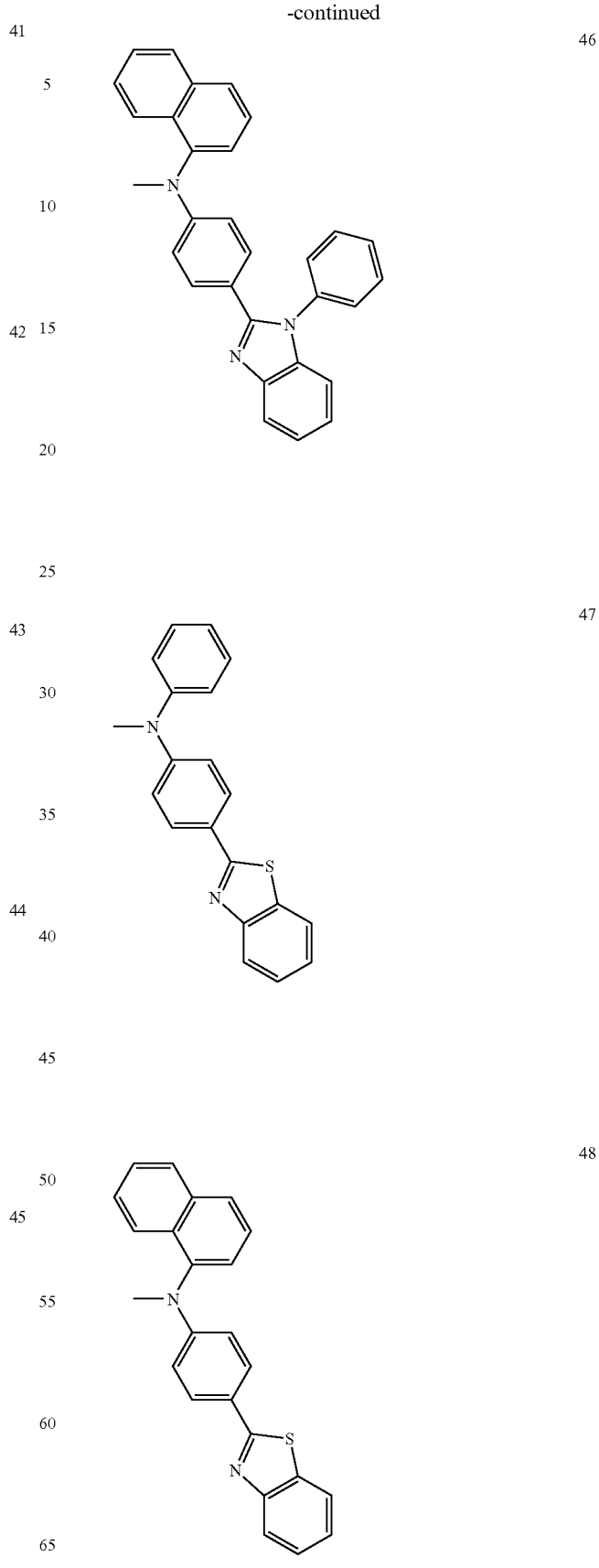

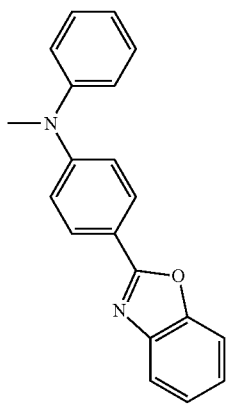
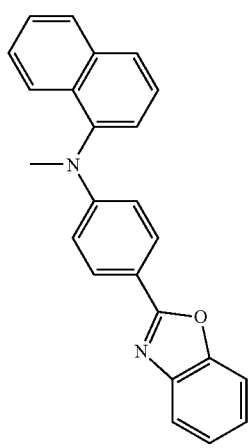
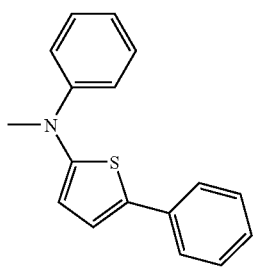
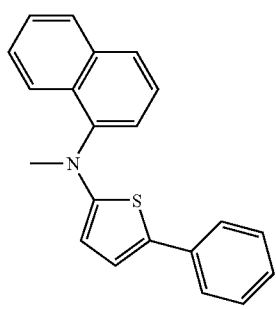
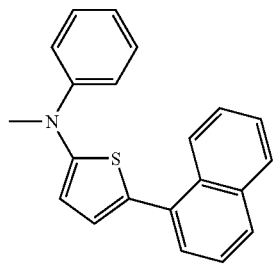
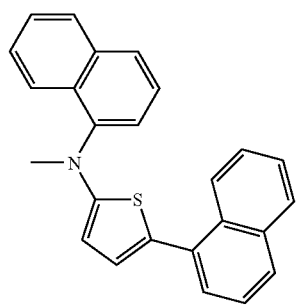
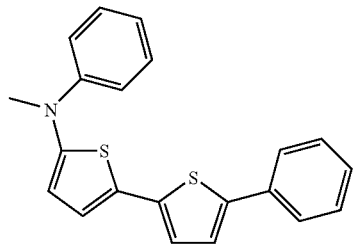
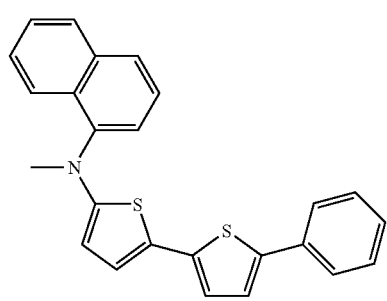
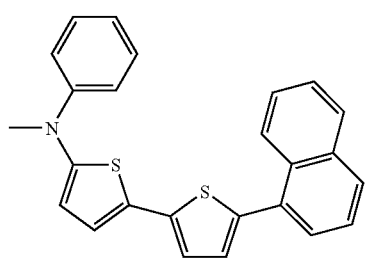

-continued

58

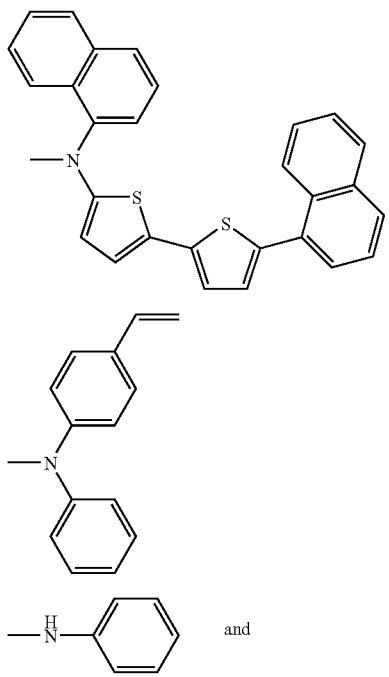

59

60 and

-continued

61

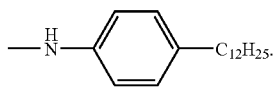

5. The organic light emitting device as set forth in claim 1, wherein the organic material layer(s) comprise a hole injection layer, and the hole injection layer includes the compound of Formula 1.

6. The organic light emitting device as set forth in claim 1, wherein the organic material layer(s) comprise a-hole transport layer, and the hole transport layer includes the compound of Formula 1.

7. The organic light emitting device as set forth in claim 1, wherein the organic material layer(s) comprise a layer which both injects and transports holes and which includes the compound of Formula 1.

8. The organic light emitting device as set forth in claim 1, comprising a homopolymer or a copolymer of the compound of Formula 1.

* * * * *